United States Patent [19]

Ehlinger

[11] 4,105,848

[45] Aug. 8, 1978

[54] PROCESS FOR THE PRODUCTION OF DIHYDROOXADIAZINONE COMPOUNDS

[75] Inventor: Robert Bruce Ehlinger, Lenox, Mass.

[73] Assignee: General Electric Company, Pittsfield, Mass.

[21] Appl. No.: 754,221

[22] Filed: Dec. 27, 1976

[51] Int. Cl.² .......................................... C07D 273/04
[52] U.S. Cl. ................................................. 544/68
[58] Field of Search ...................... 260/244 R; 544/68

[56] References Cited

PUBLICATIONS

Morrison, T. R. and Boyd, R. N., *Organic Chemistry* 3rd Edition, 1973, Allyn and Bacon Inc., pp. 503, 706–708.
Elderfield, R. C., *Heterocyclic Compounds* vol. 7, 1961, John Wiley and Sons, Inc. p. 810.

*Primary Examiner*—Henry R. Jiles
*Assistant Examiner*—R. W. Ramsuer
*Attorney, Agent, or Firm*—Morgan, Finnegan, Pine, Foley & Lee

[57] ABSTRACT

A novel process is described for the preparation of dihydrooxadiazinones by cyclizing a hydrazone under basic conditions. The hydrazones are prepared by reaction of a carbazate with an acyl alcohol that is derived from the hydrolysis of an alpha bromo precursor.

8 Claims, No Drawings

PROCESS FOR THE PRODUCTION OF DIHYDROOXADIAZINONE COMPOUNDS

This invention is concerned with the preparation of dihydrooxadiazinones by the cyclization of a hydrazone under basic conditions. The hydrazones are prepared by reaction of a carbazate with an acyl alcohol that is derived from the hydrolysis of an alpha bromo precursor.

BACKGROUND OF THE INVENTION

In copending application Ser. No. 608,450, filed Aug. 28, 1975, there are described dihydrooxadiazinone compounds and a method for their preparation. The process described in that application comprises the bromination of an appropriate alpha halo ketone that is separated from the reaction mixture prior to a separate basic hydrolysis step that is employed to prepare an acyl alcohol. Thereafter the acyl alcohol is reacted with an organocarbazate in the presence of additional acid to form a carbonorgano-oxyhydrazone that is cyclized to form the dihydrooxadiazinone under basic conditions.

It has now been found that it is possible to avoid the necessity of separating the alpha halo ketone from the reaction mixture if the reaction mixture of the alpha halo ketone is treated with an alkali metal formate in an amount that is sufficient to directly hydrolyze the alpha halo ketone to the acyl alcohol. This eliminates the need to carry out a separation step to obtain the alpha halo ketone free of hydrogen halide and of the reaction solvent. This feature is quite significant as the alpha halo ketones are potent lachrymators and special precautions are required for their handling. In addition, the present process does not require the use of additional acid in the condensation of the carbazate with the acyl alcohol as the alkali metal formate hydrolysis does not require the use of an extraneous basic reagent. The hydrolysis of the alpha halo ketone is effected with a significant reduction in high molecular weight impurities.

Accordingly, it is the primary object of this invention to provide an improved integrated process for the preparation of dihydrooxadiazinones that eliminates the need to isolate the intermediate alpha halo ketone, eliminates the use of extraneous basic reagents and reduces the number of high molecular weight impurities formed in the process.

DETAILED DESCRIPTION OF THE INVENTION

The present invention provides a process for the production of a dihydrooxadiazinone compound of the formula

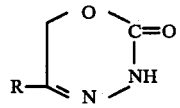

wherein R is aryl; said process comprising:

(a) brominating a compound of the formula

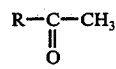

wherein R is aryl to form a mixture of

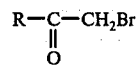

wherein R is aryl and HBr;

(b) adding to the reaction mixture of (a) an amount of an aqueous alkali metal formate that is sufficient to hydrolyze the

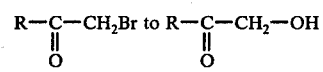

and to neutralize the HBr to formic acid and alkali metal bromide (c) adding to the reaction mixture of (b) a carbazate of the formula

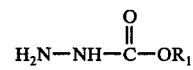

wherein $R_1$ is lower alkyl of 1 to 8 carbon atoms to form a hydrazone compound of the formula

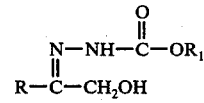

wherein R and $R_1$ are aryl; and (d) cyclizing the hydrazone of step (c) under basic conditions to form the dihydrooxadiazinone compound.

The bromination reaction may be carried out by brominating an acyl compound at a temperature in the range of from 0° C to 50° C in the presence of an effective amount i.e. 0.1-5% based on the weight of the acyl compound of a mineral acid catalyst or a Lewis Acid catalyst. Substantially stoichiometric amounts may be employed. Suitable acids include hydrochloric, sulfuric and phosphoric. The bromination may be effected in the presence of a lower alkanol. Although methanol is preferred, suitable alkanols include ethanol, propanol, butanol, pentanol, etc. After the bromination is complete, the same reactor may be directly utilized for the hydrolysis of the brominated acyl compound to form the acyl alcohol. This step may be carried out at a temperature of from about 60° C to reflux in the presence of a sufficient amount of an alkali metal formate to yield a pH in the hydrolysis reaction mixture of from 2 to 7 and more preferably from about 3 to about 3.5.

Suitable alkali metal formates include sodium formate and potassium formate. The alkali metal formate may be added first but it is preferred to first dilute the brominated reaction mixture to about 20-40, preferably about 30% solids with water. Thereafter, the alkali metal formate is added, and the mixture is agitated for from about 4 to 24-hours, preferably about 12-hours to hydrolyze the brominated acyl compound.

A carbazate, i.e. methyl carbazate is added to the reaction mixture in a substantially equal molar amount to the acyl alcohol to effect hydrazone formation. This may be done at the pH of the hydrolysis reaction which is ordinarilly acidic enough to effect this reaction at a temperature of from 20°-60° C during a 1 to 12-hour and more preferably during a 2-hour reaction cycle.

The hydrazone can be separated by a gravity separation technique such as decantation, centrifugation, filtration, etc. and the product washed with water and may be dried.

The cyclization may be carried out in a suitable organic solvent such as toluene in the presence of a basic cyclization catalyst. Suitable cyclization catalysts include sodium hydroxide, potassium carbonate, sodium carbonate, potassium hydroxide, sodium alkoxide and the like. The dihydrooxadiazinone may be recovered by allowing the mixture to cool and acidifying e.g. adding a mineral acid to the mixture with agitation. Thereafter, gravity separation techniques may be employed to separate the product.

The dihydrooxadiazinones may be employed as high temperature blowing agents for foamed plastics such as polycarbonates and polyphenylene oxides at levels of 0.1 to 1.0 part by weight per 100 parts of plastic as noted in copending Ser. No. 608,450, filed Aug. 28, 1975 which is hereby incorporated by reference.

The term aryl is employed to include phenyl, naphthyl, lower alkyl phenyl wherein the alkyl moiety has from 1 to 6 carbon atoms such as methyl, ethyl i-propyl, n-hexyl and the like; lower alkoxy phenyl wherein the alkoxy moiety has from 1 to 6 carbon atoms such as methoxy, ethoxy and the like or halophenyl such as chlorophenyl, bromophenyl and the like.

DESCRIPTION OF THE PREFERRED EMBODIMENTS

The following examples illustrate the process of the invention. These examples are not to be construed to limit the scope of the invention in any manner whatsoever:

EXAMPLE 1

A 100-gallon glass lined kettle equipped with a cooling jacket was charged with 90.5 lbs. of acetophenone, 123 lbs. of methanol and 340 mls. of 98% sulfuric acid. The reactor was cooled to 20° C and the mixture was stirred during the addition of 119 lbs. of bromine that was added incrementally by a gravity fed system at a rate so that the temperature was maintained at between 20°–25° C over a 3-hour period. After the bromination was complete, 37 lbs. of methanol, 240 lbs of water and 112 lbs. of sodium formate were added. The mixture was stirred with agitation overnight at 60° C and after cooling to 40° C a solution of 68 lbs. methyl carbazate in 45 lbs. of a 54:46 methanol-water mixture was added. The reaction mixture was stirred for 2-hours at 40° C to form the carbomethoxy nydrazone of α-hydroxy acetophenone. Thereafter the reaction mixture was allowed to cool to 20° C, was centrifuged, and washed with water on the centrifuge.

The recovered cake (116 lbs.) was added to 174 lbs. of toluene and 240 lbs. of water. The slurry was heated with agitation to 60° C and the pH was adjusted to 10.8 with sodium hydroxide (50% aq.) and stirred overnight to cyclize the carbomethoxy hydrazone to the dihydrooxadiazinone.

The mixture was cooled and acidified with 98% sulfuric acid to a pH of 3.0, and was stirred for one-half hour. Centrifugation was employed to obtain 54 lbs. of 5 - phenyl -3, 6 - dihydro - 1, 3, 4 - oxadiazinone (41% yield).

EXAMPLE 2

The following materials were combined in a 100-gallon reactor at a temperature of 16°–18° C:
  acetophenone: 90.5 lbs.
  methanol: 123 lbs.
  sulfuric acid: 340 mls.
Bromine (124 lbs) was added in the same fashion as in Example 1.

The mixture was heated upon completion of the bromine addition for 10-minutes at 30° C and cooled to 20° C to insure complete bromination. Thereafter 20 lbs. of water was added to initiate crystallization of the brominated acetophenone, 267 lbs. of water and 118 lbs. of sodium formate were also added. The reaction was held at about 70° C overnight and was then cooled to 50° C at which point 68 lbs. of methyl carbazate was added in a 54/46 mixture of methanol and water. The mixture was held at 40° C for 2 hours until the hydrazone was formed.

Thereafter water is added to kettle capacity and the mixture cooled to 20° C and stirring is continued for 1 hour.

The hydrazone is isolated by centrifugation and the solid material is formed into a slurry combined with 125 lbs. of toluene and 250 lbs. of water. One gallon of acetone was added to neutralize any remaining methyl carbazate. Agitation was applied and the reaction mixture was heated to 50°–55° C. At that point, 250 g. of hydroxyacetophenone was added to aid in the ring closure of the hydrazone and 14 lbs. of 50% aq. sodium hydroxide to give a pH greater than 10 and the mixture was stirred for 1½ hours. The solution is acidified with 98% sulfuric acid to a pH of 2.5 and cooled overnight. The mixture was centrifuged to yield the product. The cake was reslurried in 125 lbs. toluene and 250 lbs. of water, sulfuric acid was added to maintain a pH of 2.5.

The solution was stirred at room temperature for ½ to 1 hour. The solution was centrifuged to yield 68 lbs. of 5 - phenyl - 3, 6 - dihydro - 1, 3, 4 - oxadiazin-2-one.

Although the above examples have shown various modifications of the present invention, other variations are possible in light of the above teachings. It is, therefore, to be understood that changes may be made in the particular embodiments of the invention described which are within the full intended scope of the invention as defined by the appended claims.

I claim
1. A process for the production of a dihydrooxadiazinone compound of the formula

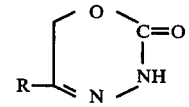

wherein R is aryl; said process comprising:
(a) brominating a compound of the formula

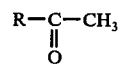

to form a mixture of

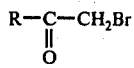

and HBr:

(b) adding to the reaction mixture of (a) an amount of an aqueous alkali metal formate that is sufficient to hydrolyze the

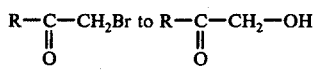

and to neutralize the HBr to formic acid and alkali metal bromide;

(c) adding to the reaction mixture of (b) a carbazate of the formula

wherein $R_1$ is lower alkyl of 1 to 8 carbon atoms to form a hydrazone compound of the formula

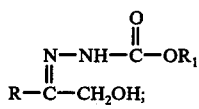

and (d) cyclizing the hydrazone of step (c) under basic conditions to form the dihydrooxadiazinone compound.

2. A process as defined in claim 1 wherein a mineral acid catalyst is added to step (a) of the reaction.

3. A process as defined in claim 2 wherein step (b) is carried out at a pH of from about 2 to about 7.

4. A process as defined in claim 3 wherein the pH is between about 3 and about 3.5.

5. A process as defined in claim 1 wherein R is phenyl.

6. A process as defined in claim 4 wherein R is phenyl.

7. A process as defined in claim 1 wherein step (d) is carried out in the presence of an alkali metal or alkaline earth metal carbonate.

8. A process for the production of 5 - phenyl - 3, 6 - dihydro - 1, 3, 4 - oxadiazin-2-one which comprises:

(a) brominating acetophenone in the presence of a mineral acid catalyst to form a reaction mixture which comprises alpha bromoacetophenone and hydrogen bromide;

(b) adding to the reaction mixture of step (a) an amount of an alkali metal formate that is sufficient to hydrolyze the alpha bromoacetophenone to form a reaction mixture containing phenacyl alcohol and to neutralize the hydrogen bromide;

(c) adding to the reaction mixture of step (b) a compound of the formula

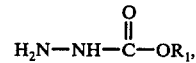

wherein $R_1$ is lower alkyl of 1 to 8 carbon atoms; to form a hydrazone compound of the formula:

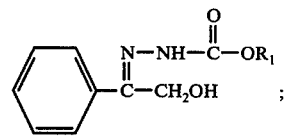

and (d) cyclizing the hydrazone of step (c) in the presence of an alkali metal or an alkaline earth metal carbonate to form 5-phenyl - 3, 6 - dihydro - 1, 3, 4 - oxadiazin-2-one.

* * * * *